United States Patent
Perlin (10) Patent No.: US 7,325,458 B2
(45) Date of Patent: Feb. 5, 2008

(54) PEAK CONTACT PRESSURE SENSOR SYSTEM (PCPSS) AND SMART BRAIN RETRACTOR SYSTEM (SBRS)

(76) Inventor: Alfred Perlin, 3382 Dato Ave., Highland Park, IL (US) 60035

( * ) Notice: Subject to any disclaimer, the term of this patent is extended or adjusted under 35 U.S.C. 154(b) by 12 days.

(21) Appl. No.: 10/924,005

(22) Filed: Aug. 23, 2004

(65) Prior Publication Data
US 2005/0043621 A1 Feb. 24, 2005

Related U.S. Application Data

(60) Provisional application No. 60/497,388, filed on Aug. 22, 2003.

(51) Int. Cl.
*G01L 7/02* (2006.01)
(52) U.S. Cl. ...................................................... 73/730
(58) Field of Classification Search .................. 73/700, 73/723, 728, 730
See application file for complete search history.

(56) References Cited

U.S. PATENT DOCUMENTS

| | | | |
|---|---|---|---|
| 2,518,906 A | 8/1950 | Kocmich | |
| 3,603,152 A * | 9/1971 | Alibert et al. | 73/723 |
| 3,960,018 A * | 6/1976 | Change et al. | 73/723 |
| 4,282,749 A | 8/1981 | Russell | |
| 5,201,325 A | 4/1993 | McEwen et al. | |
| 5,303,595 A * | 4/1994 | Shoji et al. | 73/728 |

* cited by examiner

Primary Examiner—Andre J. Allen
(74) Attorney, Agent, or Firm—Pandiscio & Pandiscio (57) ABSTRACT

A peak contact pressure sensor system comprising:
  at least one channel comprising a wall, wherein the wall is configured to deform upon engagement with a force or pressure which exceeds a threshold level, and further wherein the channel is filled with a fluid or gas; and
  a monitor for monitoring changes in the state of the fluid or gas within the at least one channel.

A smart tissue retractor system comprising: a retractor;
  at least one channel carried by the retractor and comprising a wall, wherein the wall is configured to deform upon engagement with a force which exceeds a threshold level, and further wherein the channel is filled with a fluid or gas; and
  a monitor for monitoring changes in the state of the fluid or gas within the at least one channel.

34 Claims, 8 Drawing Sheets

PCPS

Fig. 1

SOFT BRAIN SPATULA FOR DEEP AREA

| PLAIN | BLACKENED | | |
|---|---|---|---|
| 07-956-01 | 07-956-60 |  | 6mm Tip |
| 07-956-02 | 07-956-61 |  | 4mm Tip |
| 07-956-03 | 07-956-62 |  | 2mm Tip |

KUWANA SILICONIZED BRAIN SPATULA

| | | | |
|---|---|---|---|
| 07-966-01 | N/A |  | 20×220mm |
| 07-966-02 | N/A |  | 15×220mm |

KUWANA SILICONIZED BANSAN TYPE BRAIN SPATULA

| | | | |
|---|---|---|---|
| 07-967-01 | N/A |  | 18×30mm |
| 07-967-02 | N/A |  | 14×25mm |

PCPS

PCPSS

PCPS

PCPSS

PEAK CONTACT PRESSURE SENSOR SYSTEM (PCPSS) AND SMART BRAIN RETRACTOR SYSTEM (SBRS)

REFERENCE TO PENDING PRIOR PATENT APPLICATION

This patent application claims benefit of pending prior U.S. Provisional Patent Application Ser. No. 60/497,388, filed Aug. 22, 2003 by Alfred Perlin for PEAK CONTACT PRESSURE SENSOR, which patent application is hereby incorporated herein by reference.

FIELD OF THE INVENTION

This invention relates to medical apparatus and procedures in general, and more particularly to medical apparatus and procedures for engaging tissue without causing injury to the same.

BACKGROUND OF THE INVENTION

Figure 1:
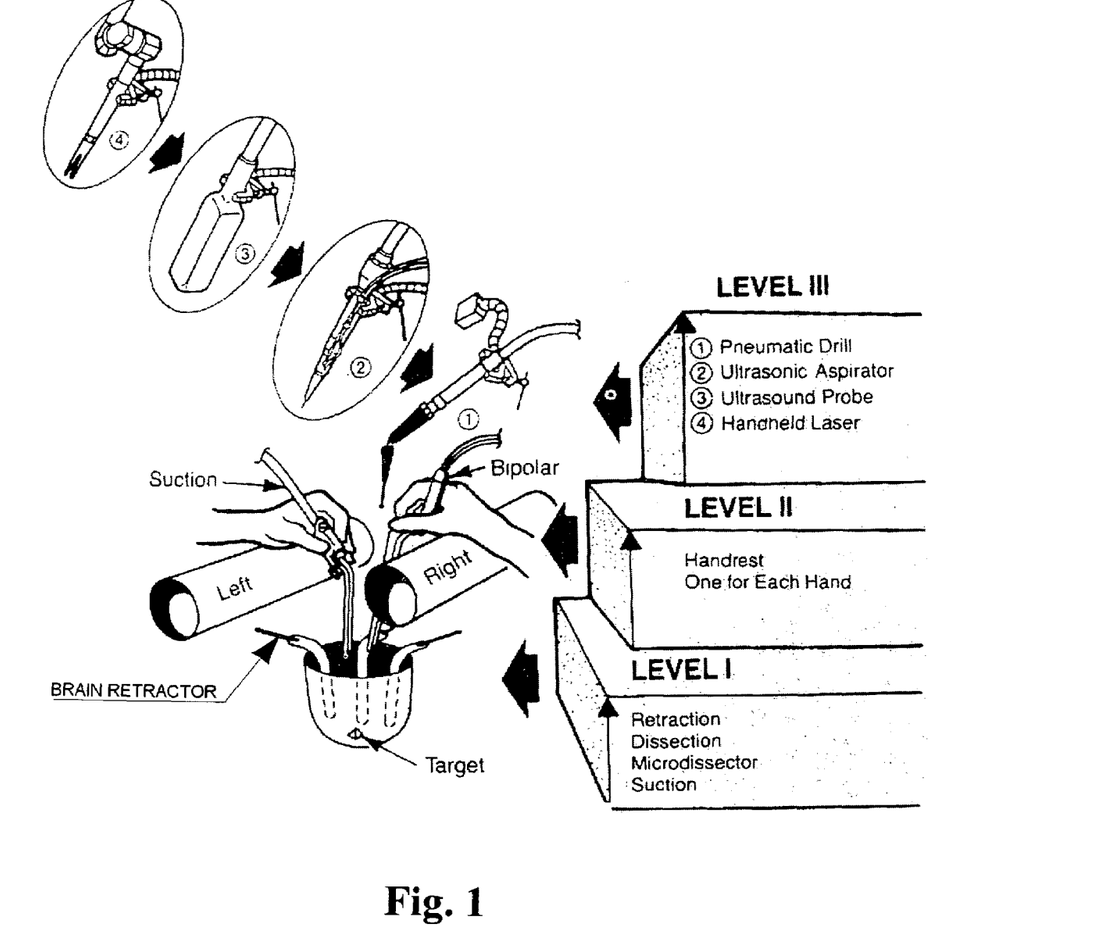
FIG. 1 is a schematic view of a surgical field including brain retractors.
Figure 2:
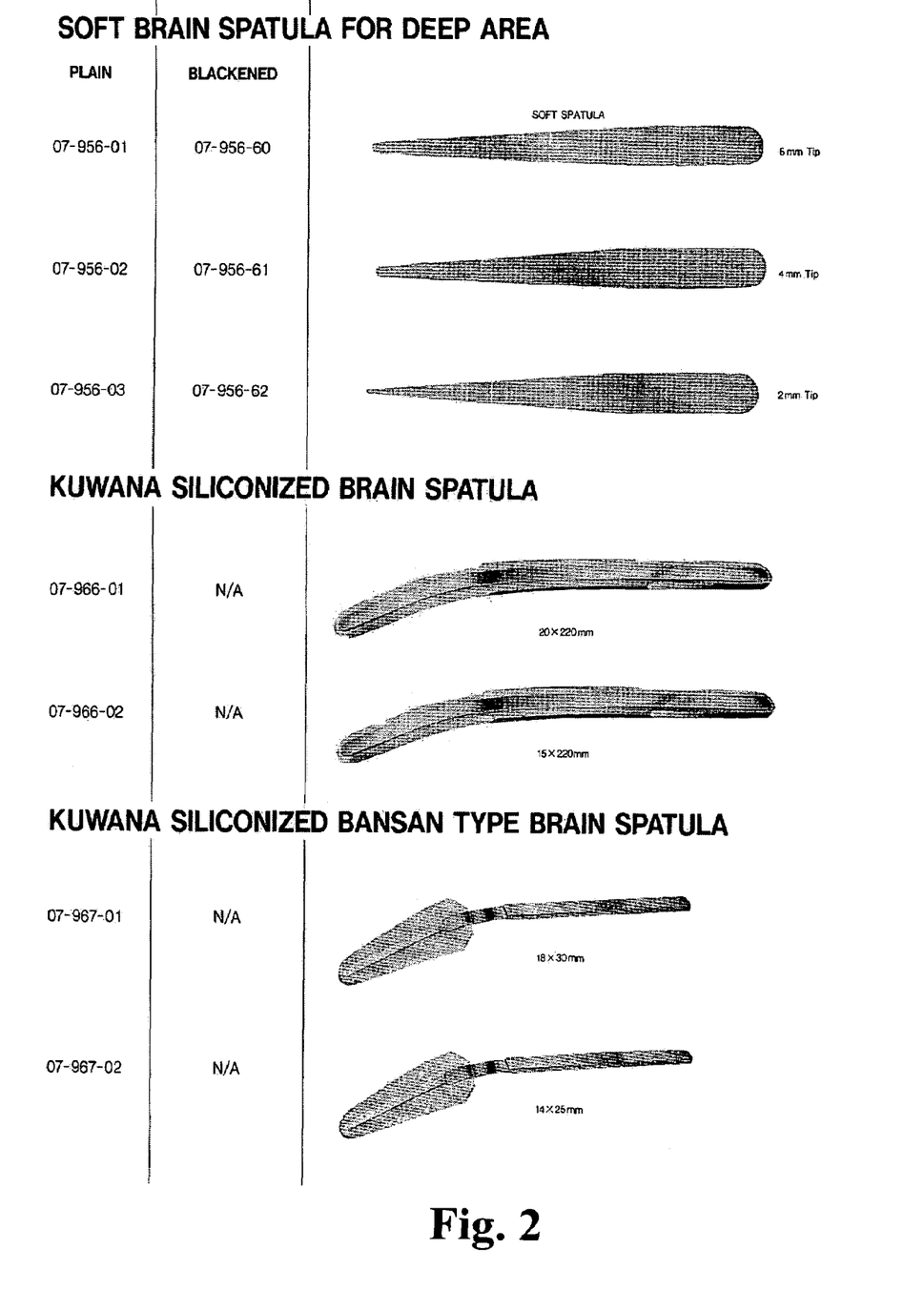
FIG. 2 illustrates various types of conventional brain retractors.

During recent years, microsurgical techniques have become increasingly common in intracranial operations, such as those involving vascular malformations, aneurysms and certain tumors, e.g., acoustic neuromas or hypophyseal tumors. In neurosurgery, during most intracranial procedures, a microscope is used to allow the surgeon to work on structures that are located deep within the brain. Under these circumstances, retraction of intervening brain tissue is generally required for adequate exposure of the target brain tissue. Numerous brain retractors of various sizes and shapes have been developed for this purpose. See FIGS. 1 and 2.

As a consequence of their function, all brain retractors must deliver some degree of pressure to the engaged brain tissue. If this pressure exceeds some level, tissue damage can occur. Depending on the degree of the tissue damage, this can result in a prolonged hospital stay, an increase in medical costs and, in many cases, impairment of neurological functions, psychiatric changes, and loss of quality of life.

More particularly, when the retractor engages the brain tissue, pressure is imposed on the engaged brain tissue, thereby causing some degree of tissue deformation and partial or total closure of blood vessels, which in turn impairs oxygen delivery to brain cells. The severity of the damage to the brain depends on various factors such as the Brain Retraction Pressure (BRP) distribution, the geometry of the brain retractor, the geometry and physical properties and type of brain tissue, the vascular pressure, the duration of the retraction, etc. In this respect it is noted that approximately 50,000 brain surgeries are performed in the United States each year which last between 30 and 45 minutes. Various studies indicate that brain tissue is likely to be negatively affected after 15 minutes of excessive retraction pressure.

Among other things, it has been found that if the Mean Arterial Pressure (MAP) exceeds the Brain Retraction Pressure (BRP) by less than 70 mm Hg, the brain will be damaged (i.e., brain damage will occur if MAP-BRP<70 mm Hg). However, it has also been found that when the difference between BRP and MAP is greater than 100 mm Hg, the brain will typically recover completely (i.e., no lasting brain damage will occur when MAP-BRP>100 mm Hg).

Furthermore, it has been found that the Regional Cerebral Blood Flow (RCBF) should be greater than 10-13 ml/100 gm/minute, otherwise there is an imminent danger of focal ischemic brain damage.

Thus, to safeguard the brain during a lengthy surgery, it is desirable that the brain retractor be provided with a means for monitoring the pressure applied to the brain tissue and for warning the surgeon if and when that pressure exceeds a maximum level.

Tissue retractors are also used in medical fields other than neurosurgery. By way of example, tissue retractors are commonly used in bladder procedures, liver vascular surgery, gynecology, organ transplantation, etc. To safeguard these other tissues during such procedures, it is also desirable that such other tissue retractors be provided with a means for monitoring the pressure applied to the tissue and for warning the surgeon if and when that pressure exceeds a maximum level.

SUMMARY OF THE INVENTION

These and other objects are addressed by the present invention which, in one form of the invention, comprises a Smart Brain Retractor System (SBRS), comprising a Peak Contact Pressure Sensor System (PCPSS), which monitors the pressure applied to the tissue by the retractor, and which activates an alarm when pressure above a selected level is applied to the tissue.

More particularly, the Smart Brain Retractor System (SBRS) comprises a retractor and the Peak Contact Pressure Sensor System (PCPSS). Peak Contact Pressure Sensor System (PCPSS) in turn comprises a Peak Contact Pressure Sensor (PCPS) and a monitor for monitoring the peak contact pressure detected by the PCPS. The Peak Contact Pressure Sensor (PCPS) is mounted to the retractor and the monitor monitors the peak contact pressure at the retractor surface when the retractor engages anatomical tissue.

Similar smart retractors may be provided for use with anatomical tissues other than the brain.

Stated another way, the present invention provides a safe and reliable system for monitoring the pressure exerted on tissue by a retractor element so as to minimize injury to the patient. In one form of the invention, there is provided a novel Smart Brain Retractor System (SBRS) equipped with a unique Peak Contact Pressure Sensor System (PCPSS). During tissue retraction or other procedure which requires handling of tissue, the PCPSS continuously monitors the contact pressure between the retractor and the tissue, and activates an alarm if and when the pressure exceeds a threshold level. Significantly, the PCPSS can be used with substantially any retractor; it is inexpensive and simple to use; it may be made so as to be at least in part disposable; and it has no electrical connections adjacent the tissue. The Peak Contact Pressure Sensor System (PCPSS) comprises Peak Contact Pressure Sensor (PCPS), which in turn comprises a network of flexible, gas-filled channels which engage the tissue during retraction. These flexible channels are configured so that they will deform at a contact pressure or force which is lower than a pre-determined level, i.e., one which could damage the tissue. For example, this pre-determined pressure level might be the contact pressure required to occlude blood vessels in the retracted tissue. The Peak Contact Pressure Sensor System (PCPSS) also comprises a monitor for monitoring the parameters of the gas within the channels, e.g., flow rate, pressure, etc. When the flexible, gas-filled channels deform, gas flow through the channels and/or pressure within the channels is significantly altered, whereupon the monitor can activate an alarm to alert the surgeon that the contact pressure has exceeded a safe level.

The Peak Contact Pressure Sensor System (PCPSS) monitor can be programmed with patient data, and it can also gather important patient-specific physiological parameters (e.g., arterial blood pressure, core temperature, elapsed time, etc.), and adjust the gas flow and/or pressure in the sensor channels accordingly.

In one form of the invention, there is provided a peak contact pressure sensor comprising:

at least one channel comprising a wall, wherein the wall is configured to deform upon engagement with pressure or a force which exceeds a threshold level, and further wherein the channel is filled with a fluid or gas.

In another form of the invention, there is provided a peak contact pressure sensor system comprising:

at least one channel comprising a wall, wherein the wall is configured to deform upon engagement with a pressure or force which exceeds a threshold level, and further wherein the channel is filled with a fluid or gas; and a monitor for monitoring changes in the state of the fluid within the at least one channel.

In another form of the invention, there is provided a smart tissue retractor system comprising:

a retractor;

at least one channel carried by the retractor and comprising a wall, wherein the wall is configured to deform upon engagement with a pressure or force which exceeds a threshold level, and further wherein the channel is filled with a fluid or gas; and a monitor for monitoring changes in the state of the fluid or gas within the at least one channel.

In another form of the invention, there is provided a method for measuring a pressure or force applied to a first object by a second object, the method comprising:

providing at least one channel comprising a wall, wherein the wall is configured to deform upon engagement with a force which exceeds a threshold level, and further wherein the channel is filled with a fluid or gas;

positioning the at least one channel on the first object so that the wall will engage second object; and monitoring changes in the state of the fluid within the at least one channel.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein.

In the accompanying drawings, the following alphanumerics are intended to denote the following elements:

PCPS is intended to denote the Peak Contact Pressure Sensor (PCPS);

PCPSS is intended to denote the Peak Contact Pressure Sensor System (PCPSS);

SBRS is intended to denote the Smart Brain Retractor System (SBRS);

1 is intended to denote the gas-filled channels in the Peak Contact Pressure Sensor (PCPS);

2 is intended to denote the inlet to the channels 1;

3 is intended to denote the pressurized gas source connected to inlet 2;

4 is intended to denote the compressor for pressurizing the pressurized gas source 3;

5 is intended to denote the pressure transducer for reading the pressure in pressurized gas source 3;

6 is intended to denote the regulator placed between pressurized gas source 3 and inlet 2;

7 is intended to denote a flow restriction downstream of channels 1;

8 is intended to denote the monitor for detecting air flow at the output of channels 1;

9 is intended to denote the pressure transducer for reading the pressure between inlet 2 and regulator 6;

10 is intended to denote the outlet from channels 1;

11 is intended to denote the control unit which may be included in monitor 8;

12 is intended to denote the pressure transducer for determining the patient's arterial pressure;

13, 14 and 15 are intended to denote elements which may be used to form the Peak Contact Pressure Sensor (PCPS), wherein 13 denotes the inner wall of the Peak Contact Pressure Sensor (PCPS), 14 denotes the outer wall of the Peak Contact Pressure Sensor (PCPS), and 15 denotes an internal member defining the channel pathways (alternatively, the internal member 15 may be omitted altogether and the channels 1 defined by selected joining of outer wall 14 to inner wall 13, e.g., by welding or gluing); and

16 is intended to denote anatomical retractor, e.g., a brain retractor in the case of the Smart Brain Retractor System (SBRS).

DETAILED DESCRIPTION OF THE PREFERRED EMBODIMENTS

Overview

The Smart Brain Retractor System (SBRS) comprises a Peak Contact Pressure Sensor System (PCPSS). During tissue retraction, the Peak Contact Pressure Sensor System (PCPSS) continuously monitors the contact pressure between the retractor and the tissue, and activates an alarm if and when the pressure exceeds a threshold level.

The Peak Contact Pressure Sensor System (PCPSS) comprises a network of flexible, gas-filled channels which engage the tissue during retraction, and a monitor for monitoring the gas flow through those channels and/or the gas pressure within those channels. The flexible channels are configured so that they will deform at a contact pressure which is lower than a threshold pressure level, i.e., one which could damage the tissue. When the flexible, gas-filled channels deform due to excessive contact pressure between the retractor and the tissue, gas flow through the channels and/or pressure within the channels is altered, whereupon the monitor activates an alarm to alert the surgeon.

It should be appreciated that in one embodiment of the present invention, the channels are configured so that they deform when the contact pressure exceeds a threshold value, thereby altering the pressure and/or flow of the gas inside the channels. In this embodiment, the monitor monitors a change in the pressure and/or flow of the gas within the deformed channel.

In one preferred embodiment of the present invention, the channels are configured to fully collapse when the retraction pressure exceeds a pre-determined level. In this embodiment, when the contact pressure exceeds the pre-determined level, the channels fully collapse and take the shape of the retractor blade and the flow of the gas is substantially fully stopped. In such a case, the monitor detects the absence of gas flow through the collapsed channel, or a changed gas pressure, which in turn activates an alarm.

Behavior of Thin Wall Bladders or Tubes

Pneumatic devices such as an inflatable bladder, as well as the Peak Contact Pressure Sensor System (PCPSS) of the present invention, are based on the behavior of collapsible thin wall bladders or tubes. Their approximate behavior is based on Laplace's formula, which describes the behavior of thin elastic membranes (i.e., ideally, walls that have zero thickness). This law describes shape (represented by radius R) under which tension forces (causing stretching of the curved thin wall segment) can balance the forces resulting from pressure difference across the segment, namely, $$R = T/(Pi - Pe) \text{ or } Pi - Pe = T/R \tag{a}$$

where Pi is the internal pressure, Pe is the external pressure, T is the tension that stretches the segment and R is the radius of the curvature of the segment. According to this law, the pressure on both sides of the membrane wall must be equal (Pi=Pe) if: (i) in the case where small and thin bladders are used for pressure measurement, the radius of curvature R is infinite, which means that the segment is flat; or (ii) in the case where the wall segment is not under tension (i.e., T=0).

When T is greater then zero, and the internal pressure is greater then the external pressure, the bladder has a defined shape (i.e., R is positive). Consider a bladder with membrane-like walls. In such a case, the membrane walls cannot physically have negative radius of curvature (i.e., R<0). In addition, the membrane can be stretched (i.e., T is positive) and can never be compressed (i.e., T is negative). If one tries to compress the membrane, it will only bend. Then, in the case of a membrane-made bladder, according to Laplace's formula, when the external pressure is greater than the internal pressure, the membrane walls will not have a defined shape (i.e., R cannot be negative). Under those conditions, the bladder will take the shape of its support surface, with the walls attached to one another (i.e., the bladder is collapsed). This condition, in a case of collapsed tube, means that the cross-section will be equal to zero and no gas will flow through it.

In cases of bladders and tubes made of very thin elastic materials, Laplace's formula is only an approximation. It means that a collapse will occur when the external pressure will exceed the internal pressure by a certain amount. This difference can be found experimentally.

From this discussion, it will be seen that the Peak Contact Pressure Sensor (PCPS) channels will collapse when the external pressure exceeds the internal pressure by a selected amount. In addition, the Peak Contact Pressure Sensor (PCPS) channel will take the shape of the retractor blade and the flow of gas will be impeded.

Behavior of Collapsible Thin Wall Tubes

With the Peak Contact Pressure Sensor (PCPS), since there is no outlet for the gas, the whole inner space of the channels will be pressurized to the same pressure as the pressure source (Po). The time needed for this to occur depends on the pressure difference between the inlet and outlet (Pdiff), gas viscosity (u) and gas density (Ro), and especially on the volume of the channel. This means that the Peak Contact Pressure Sensor (PCPS) will perform well in a case of very long channels, but the response time will be increased.

There are two methods for detecting a total collapse of the walls of the channel. One method depends on monitoring of the pressure and the other method depends on monitoring of the flow.

In a totally collapsed channel, the volume rate of the flow (Q) is equal to zero and the inlet pressure is equal to maximum pressure=Po.

In the case of pressure monitoring, the total pressure can be considered to be equal to the sum of the static and dynamic pressures (Ptot=Pst+Pdyn).

The dynamic pressure is given by:

$$Pdyn = 1/2 * Ro * (V)^2 \tag{b}$$

where V is mean velocity of the gas. Consider what happens when gas flows in laminar fashion through a collapsible round tube (i.e., channel). Before collapse, according to the Hagen-Poiseuille Law:

$$Q = C_1 * R^4 / (u * L) * dP \tag{c}$$

and $$V = Q/(3.14 * R^2) \tag{d}$$

where Q is the volume rate of flow, C, is a coefficient, R is radius and L is length of the tube, and P is the pressure difference between the inlet and outlet, and in this case it equals:

$$dP = Pi - Patm \tag{e}$$

Assume that a cross-section of the collapsible channel is determined from the geometry of the retractor to which the channel is attached. In such case, instead of the radius of a round channel R in Equations (c) and (d), one can use an equivalent radius (Req).

Consider what happens to a sensor at the inlet to the channel after the tube collapses and gas flow is blocked. In the present system, the pressure sensors may be configured to sense only the static pressure. When the channel is blocked, there is no gas flow and the static pressure in the whole channel is equal to the total pressure in the reservoir:

$$Pbl = Pst = Pi = Po \tag{f}$$

When gas flows through the channel, the pressure sensor at the inlet will sense $$Pop = Pst = Po - Pdyn. \quad (g)$$

Thus, $$Pdiff = Pbl - Pop - Pdyn \quad (h)$$

By combining Equations (b) through (h), a first order approximation may be derived for the case of a collapsible round channel. The pressure difference that the inlet sensor will sense between open and blocked channel (Pdiff) is:

$$Pdiff = C_2 * (Ro/u^2) * (Req^4 l/L^2) * dp^2 \quad (i)$$

From Equation (i), it will be seen that Pdiff should represent a range of pressure sensor values (Prng). For a given pressure sensor, the maximal channel length ($L^{max}$) or the maximal equivalent radius ($Req^{max}$) is:

$$R_{eq}^{max} = C3 * (Prng/Ro)^{1/4} * (L * u/dP)^{1/2}$$

$$\text{and } L^{max} = C4 * (Ro/Prng)^{1/4} * (dP/u) * Req^2 \quad (j)$$

And for a case of air flow:

$$R_{eq}^{max} = C5 * Prng^{1/4} * (L/(Po - Patm))^{1/2}$$

$$\text{and } L^{max} = C6 * Req^2 * (Po - Patm)/Prng^{1/2} \quad (k)$$

In the case that the action of the Peak Contact Pressure Sensor System (PCPSS) depends on a gas flow sensor, similar analysis can be given as $L^{max}$ and $Req^{max}$. In this case, when Qrng represents the sensing range of flow sensor, Equation (c) will yield $$R_{eq}^{max} = C7 * (Qrng * u * L/dP)^{1/4}$$

$$\text{and } L^{max} = C8 * dP/Qrng/u * Req^4 \quad (l)$$

Or, for a case of air, $$R_{eq}^{max} = C9 * (Qrng * L/(Po - Patm))^{1/4}$$

$$\text{and } L^{max} = C10 * (Po - Patm)/Qrng * Req^4 \quad (m)$$

It should be appreciated that all of the foregoing equations are written for the theoretical case of channels whose walls are made of membranes. In such a case, the reservoir Po has to be equal to the maximum retraction pressure $Pt^{max}$ ($Po = Pt^{max} = Pi$). Since the range of detectors Prng and Qrng are given, one can find the maximum length of the channel (Lmax) after assuming the value of Req. Or, after assuming the value of channel length L, Req can be calculated.

In practice, it may be desirable to include additional influences such as stiffness of the channel walls, geometry of the channel and the physical properties of the gas. This is done with the help of the constants C1 through C10 specified above.

Peak Contact Pressure Sensor System (PCPSS)

The Peak Contact Pressure Sensor System (PCPSS) of the present invention operates on the principle of collapsible channels. A simplified model of such a sensor system can be described as a long channel with thin elastic walls through which the gas flows from a constant but adjustable pressure source. If the pressure acting on the outside of any segment of the wall is increased, it will cause this segment of the channel to collapse. According to the Laplace's formula set forth in the Equation (a) above, the collapse will occur at the wall location where the external pressure is greater than the internal pressure. Such local collapse of the channel causes the flow resistance of the channel to increase sharply. Such increase of the flow resistance of the channel in turn leads to significant decrease of gas flow through the channel. As described in the aforementioned "idealized" case of the inflatable bladder, a sudden change of geometry of a segment of the channel (which involves flattening of the thin wall) indicates that the outside pressure is greater than the inside pressure.

One significant advantage of the Peak Contact Pressure Sensor System (PCPSS) is that it detects not the mean pressure, but the maximum pressure, anywhere along the entire length of the channel. Therefore, by forming a channel in such a way that it covers a specific surface area of the retracted tissue, a sensor can be constructed that detects the highest pressure anywhere on the surface which is in contact with the outer wall of the channel.

When the surface of the brain retractor is small, a single channel may be able to detect the highest pressure over the area of the retracted tissue; however, where the surface of the brain retractor is large, the Peak Contact Pressure Sensor System (PCPSS) may contain a plurality of independent channels so as to enable coverage over the entire area of the retracted tissue.

In addition to the foregoing, it should be appreciated that the plurality of independent channels may deform at a plurality of locations over the entire tissue surface adjacent to the surface of the brain retractor. In such a case, the monitor will respond as soon as any one peak pressure exceeds the predetermined threshold value and then activate an alarm to alert the surgeon.

Significantly, the idea of applying Laplace's formula in the channels of the Peak Contact Pressure Sensor System (PCPSS) to monitor the contact pressure between the retractor and the tissue is somewhat analogous to what happens to the brain tissue during the process of tissue retraction. Inside the tissue, there is a system of blood vessels. When sufficiently high external pressure is applied to the tissue, the blood vessels collapse and blood flow is stopped. In the novel brain retractor of the present invention, the retracting surface of the retractor is covered with a system of channels through which a gas flows. The brain retractor channel system is configured so that, during retraction, the retractor channel system will collapse before the blood capillaries collapse and brain damage occurs.

In a preferred form of the present invention, the channel system of the retractor can include a plurality of channels which can be arranged in parallel configurations. If needed, several independent Peak Contact Pressure Sensors (PCPS's) can be mounted on the active part of the retractor. The number of pressure detectors mounted on the retractor will generally depend on the geometry of the retractor and the sensitivity desired for the system.

As described above, the present invention provides a system for monitoring the pressure exerted on tissue by a retractor element so as to minimize injury to the patient. Among other things, the new Peak Contact Pressure Sensor System (PCPSS) has the following significant features:

1. The new Peak Contact Pressure Sensor System (PCPSS) provides a warning before the condition of the retracted tissue becomes dangerous. In case when retraction pressure is greater then MAP, smart brain retractor system can provide surgeon with estimate how long it will take for patient to develop permanent damage if current retraction pressure will be maintained.

2. The Peak Contact Pressure Sensor System (PCPSS) and Smart Brain Retractor System (SBRS) are non-electrical at the surgical site.

3. The high pressure warning provided by the system is based on the condition of the entire portion of the brain retractor covered by the channels in contact with the tissue, including the leading edges of the brain retractor.

4. The Peak Contact Pressure Sensor System (PCPSS) and Smart Brain Retractor System (SBRS) are both flexible, which allows the surgeon to adjust the configuration of the retractor blade.

5. The warning can be based not only on the retraction pressure, but also on additional physiological characteristics, e.g., mean arterial pressure, elapsed time, etc.

6. The Peak Contact Pressure Sensor System (PCPSS) and Smart Brain Retractor System (SBRS) both comprise disposable parts which makes them is inexpensive and simple to use. Additionally, the reusable working portion of the Smart Brain Retractor System (SBRS) (i.e., the spatula) may be made out of metal, and thus can be easily sterilized (autoclaved).

7. If desired, brain moisturizing channels may be added to the system, whereby to eliminate the use of cotton sponges.

The Peak Contact Pressure Sensor System (PCPSS)

Figure 3:
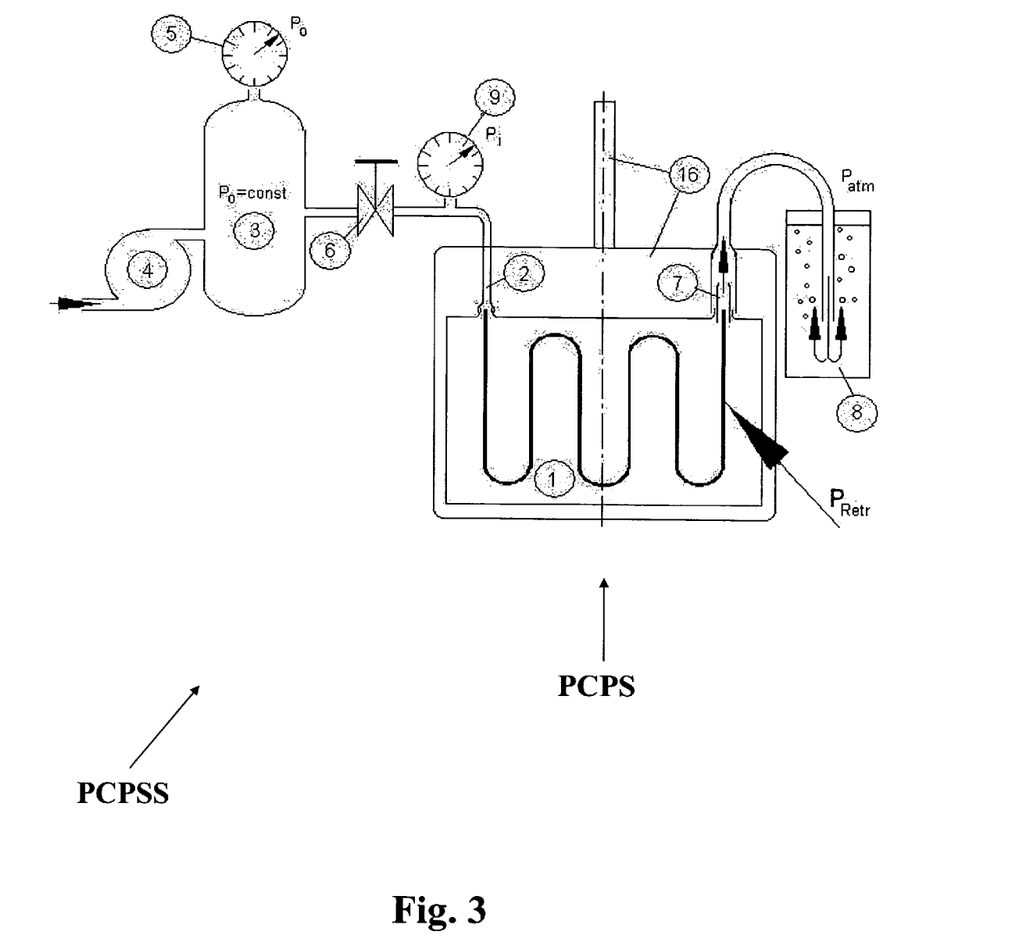
FIG. 3 is a schematic view of a simple Peak Contact Pressure Sensor System (PCPSS) formed in accordance with the present invention which uses water as a gas flow detector.
Figure 4:
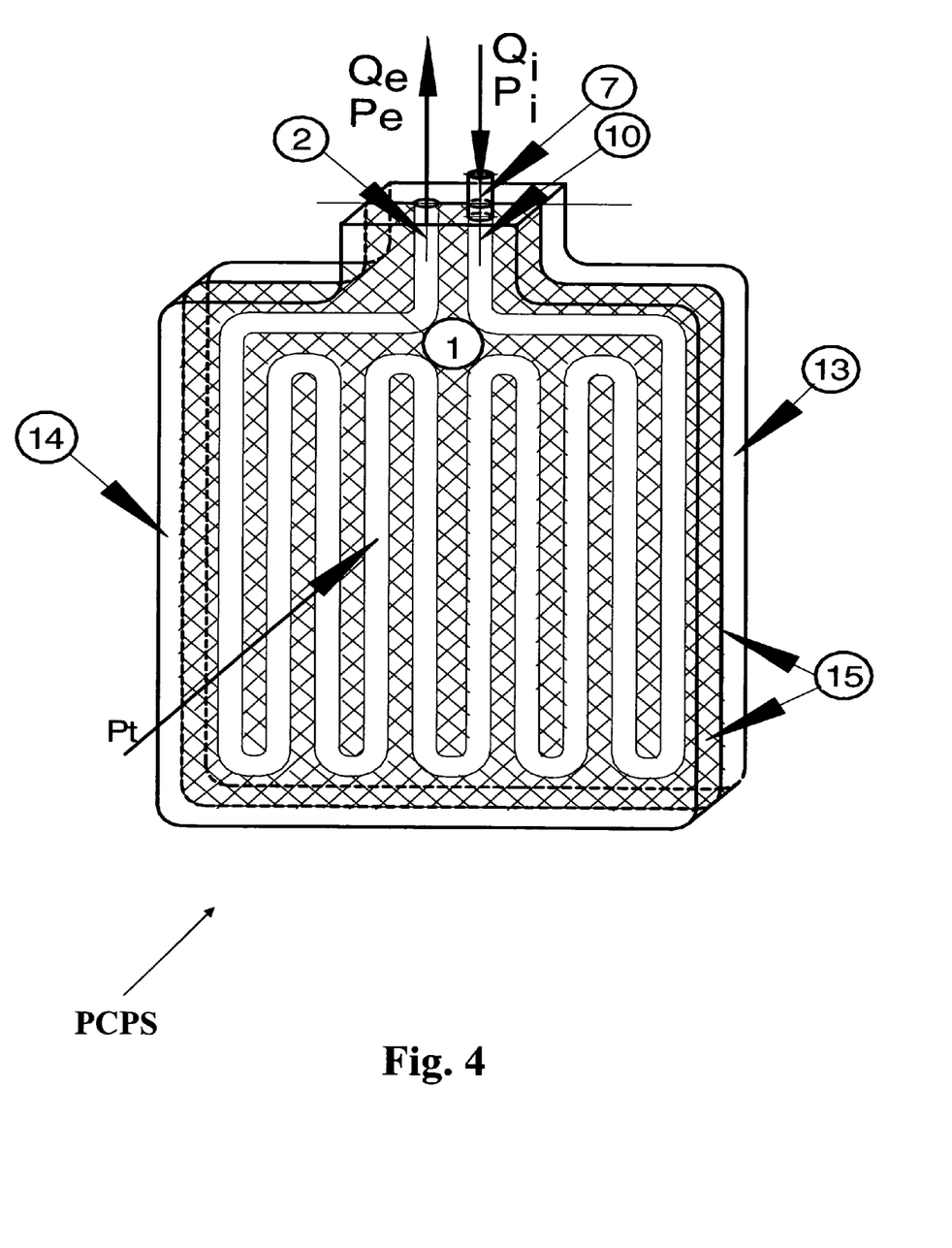
FIG. 4 is a schematic view of an exemplary Peak Contact Pressure Sensor (PCPS) formed in accordance with the present invention.

Looking now at FIGS. 3 and 4, there is shown one preferred form of the Peak Contact Pressure Sensor System (PCPSS). It comprises a Peak Contact Pressure Sensor (PCPS) which may be formed using two biocompatible thin plastic sheets or walls 13 and 14. Sheets 13 and 14 are fused or glued on either side of internal member 15 which defines the channel pathways, whereby to form a network of collapsible gas channels 1. Alternatively, the internal member 15 may be omitted altogether and the channels 1 defined by selected joining of outer wall 14 to inner wall 13 e.g., by welding or gluing. The gas flows from inlet 2 through a maze of channels 1 and toward outlet 10 and exits through a restriction 7. When the external retraction pressure (Pt), which acts on any segment of collapsible channels 1, is greater than the internal pressure of the gas inside channels 1 (Pi), the channel deforms and the physical characteristics of the gas flow change. These changes are detected by monitor 8. In one preferred embodiment of the present invention, the channel collapses completely and prevents the gas from flowing altogether.

The Peak Contact Pressure Sensor (PCPS) is intended to be used in conjunction with a monitor for monitoring changes in the state of the gas within channels 1, whereby to form the complete Peak Contact Pressure Sensor System (PCPSS).

Preferably, the Peak Contact Pressure Sensor (PCPS) is attached to the working surface of a commercially available brain retractor 16 whereby to form, in conjunction with the gas monitor, the Smart Brain Retractor System (SBRS). The system also comprises air compressor 4, which pressurizes the tank 3 to maximum pressure Po. The air from the tank flows through regulator 6 and is reduced to constant pressure Pi. In a preferred form of the invention, all these components are built so as to create an Adjustable Air Source (AAS) unit.

In the simple Peak Contact Pressure Sensor System (PCPSS) shown in FIG. 3, the inlet tube 2 is connected to the Adjustable Air Source (AAS) unit which supplies the constant pressure Pi. The gas flows through the collapsible channels 1 formed in the Peak Contact Pressure Sensor (PCPS) and escapes from the outlet tube 10 through a flow restriction 7. Restriction 7 acts as a flow resistor and can be in the form of a small orifice, obstruction or filter.

In one form of the present invention, restriction (or flow resistance) 7 is created by submerging the output tube 10 in water to a depth h. At the same time, submerging the output tube 10 in the water acts as an air flow detector 8 (i.e., due the visual appearance of bubbles in the water). More particularly, when the gas flows out of output tube 10 and into the water, air bubbles are formed in the water. The absence of the bubbles coming out of the tube indicates that the air channel has collapsed and the retraction pressure Pt is greater than the pressure Pi inside channel 1. Therefore, placing output tube 10 in the water provides a simple yet highly effective air flow detector 8.

If desired, the Peak Contact Pressure Sensor System (PCPSS) may pressurize its channels 1 with ordinary ambient air, however, better results may be obtained by using a lower viscosity gas, e.g., $CO_2$.

Figure 5:
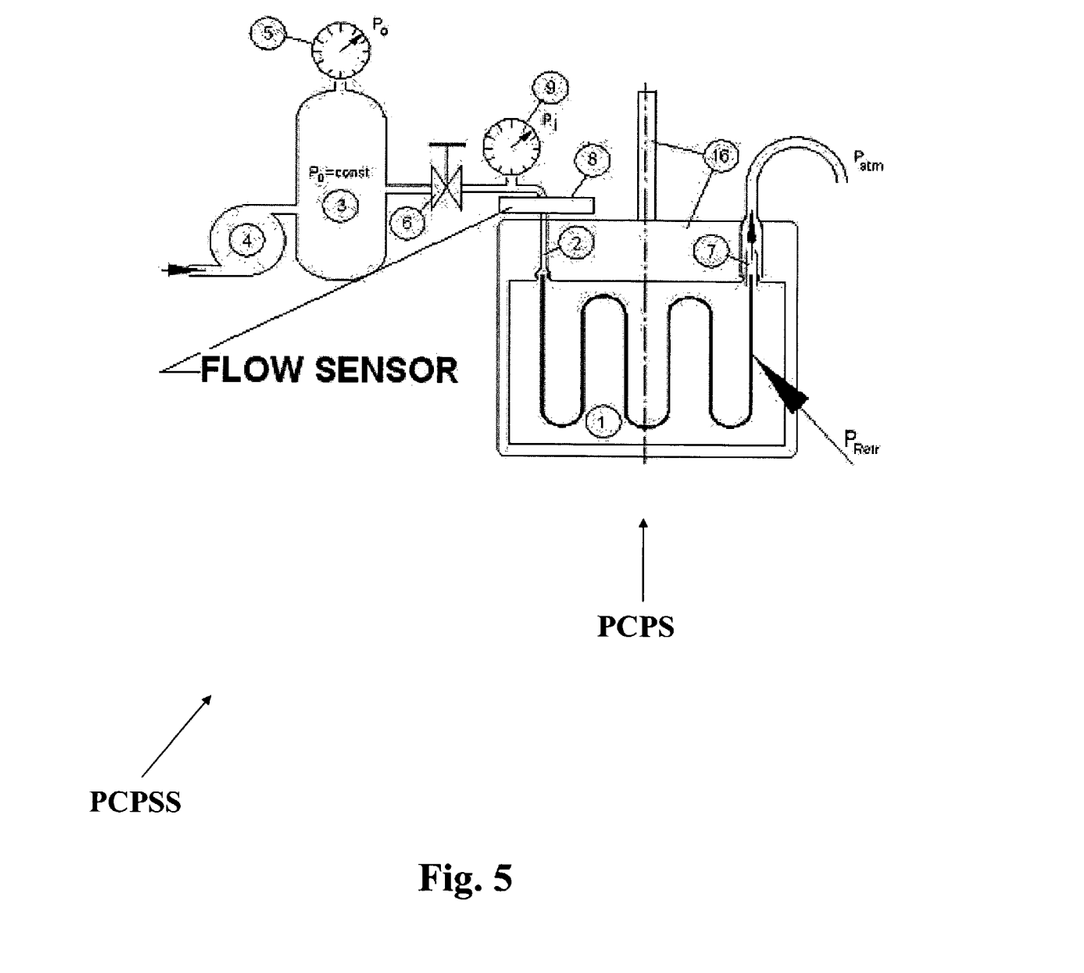
FIG. 5 is a schematic view of an alternative Peak Contact Pressure Sensor System (PCPSS) formed in accordance with the present invention which uses a flow sensor upstream of the Peak Contact Pressure Sensor (PCPS)

FIG. 5 shows a system similar to that shown in FIG. 4, except that the gas flow sensor 8 is now located between the pressurized gas source 3 and the inlet 2 to channels 1. In this construction, outlet tube 10 simply vents to the atmosphere.

Figure 6:
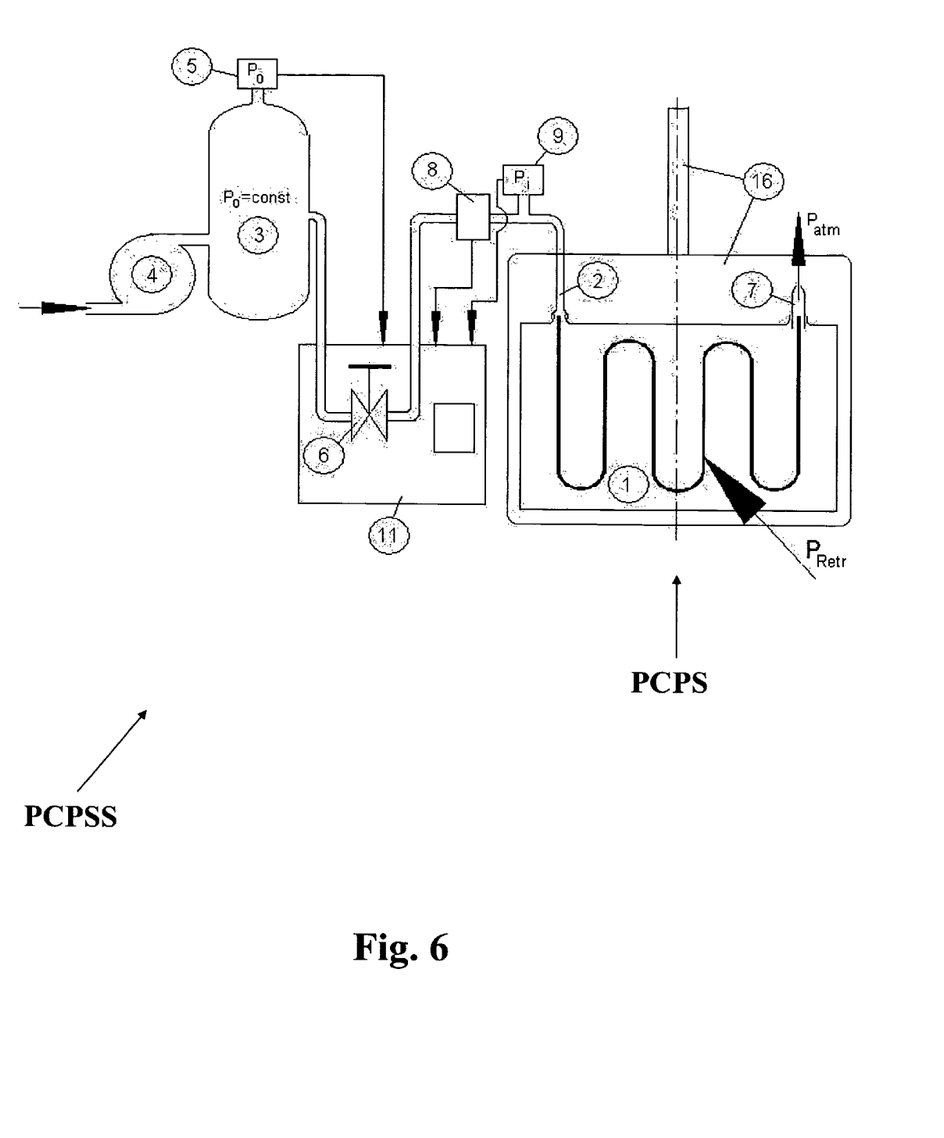
FIG. 6 is a schematic view of an advanced Peak Contact Pressure Sensor System (PCPSS) formed in accordance with the present invention which also utilizes flow sensor upstream of the Peak Contact Pressure Sensor (PCPS)

An advanced Peak Contact Pressure Sensor System (PCPSS) is shown in FIG. 6. Peak Contact Pressure Sensor System (PCPSS) comprises an Adjustable Air Source (AAS) unit, electronic pressure sensor 9 and gas flow sensor 8. In this construction, the gas flow sensor 8 is connected to the inlet 2 of the Peak Contact Pressure Sensor (PCPS) which is mounted on the brain retractor 16. The gas from the Peak Contact Pressure Sensor (PCPS) escapes to the atmosphere through the flow restrictor 7. When the outside pressure Pt acting on the surface of the Peak Contact Pressure Sensor (PCPS) and its channels becomes greater than the internal pressure Pi, gas flow sensor 8 senses a sudden change in the gas flow rate and sends a signal to the control unit 11, which activates an alarm. In addition, control unit 11 receives and displays signals from electronic pressure transducers 5 and 9.

Figure 7:
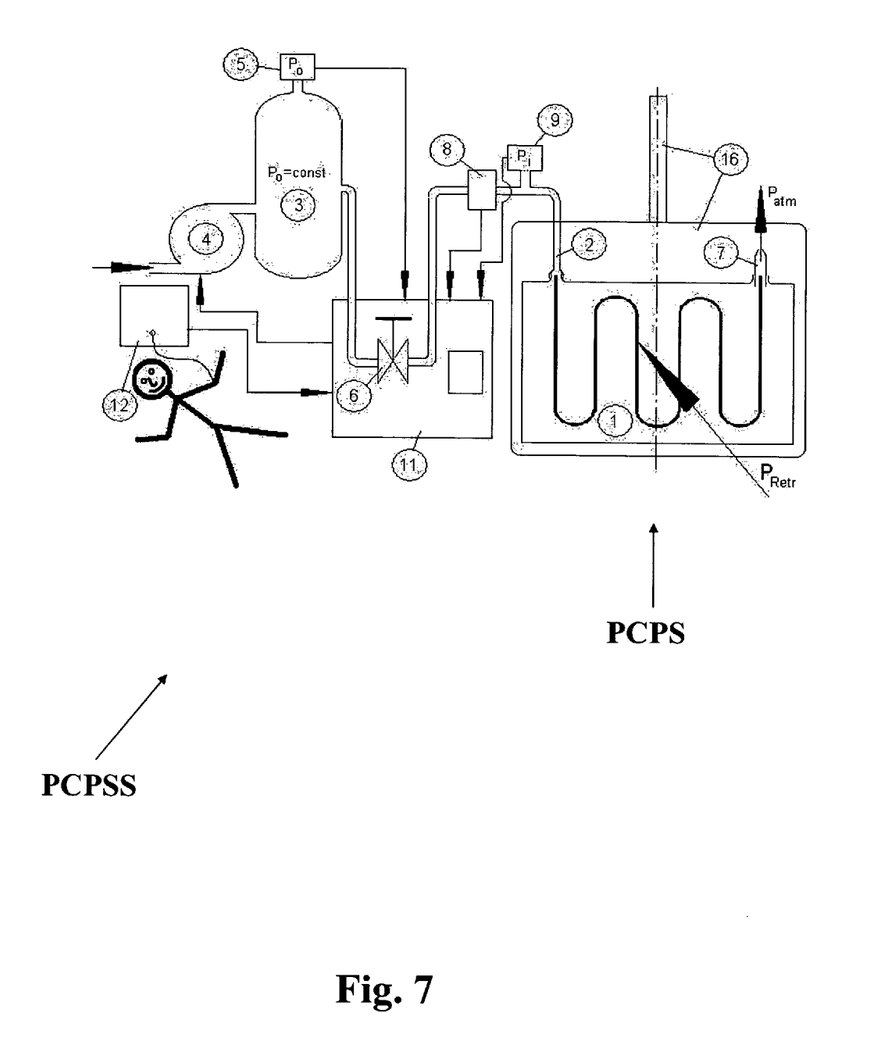
FIG. 7 is a schematic view of still another alternative Peak Contact Pressure Sensor System (PCPSS) formed in accordance with the present invention which uses a flow sensor upstream of the Peak Contact Pressure Sensor (PCPS) and data from the patient.

The advanced Smart Brain Retractor System (SBRS) is shown in FIG. 7. In this construction, the Peak Contact Pressure Sensor (PCPS) is connected to the control unit 11, which gathers data from a flow meter 8, from the patient's arterial blood pressure transducer 12 and from gas pressure sensors 5 and 9. Using the reading from pressure sensor 5, the microprocessor can control the air compressor 4, whereby to keep the pressure Po constant at a desired level. In addition to monitoring the aforementioned parameters, other important physical and physiological parameters can be monitored by control unit 11. In addition, elapsed time can be monitored as well; this can be significant inasmuch as many forms of tissue damage are time dependent.

Figure 8:
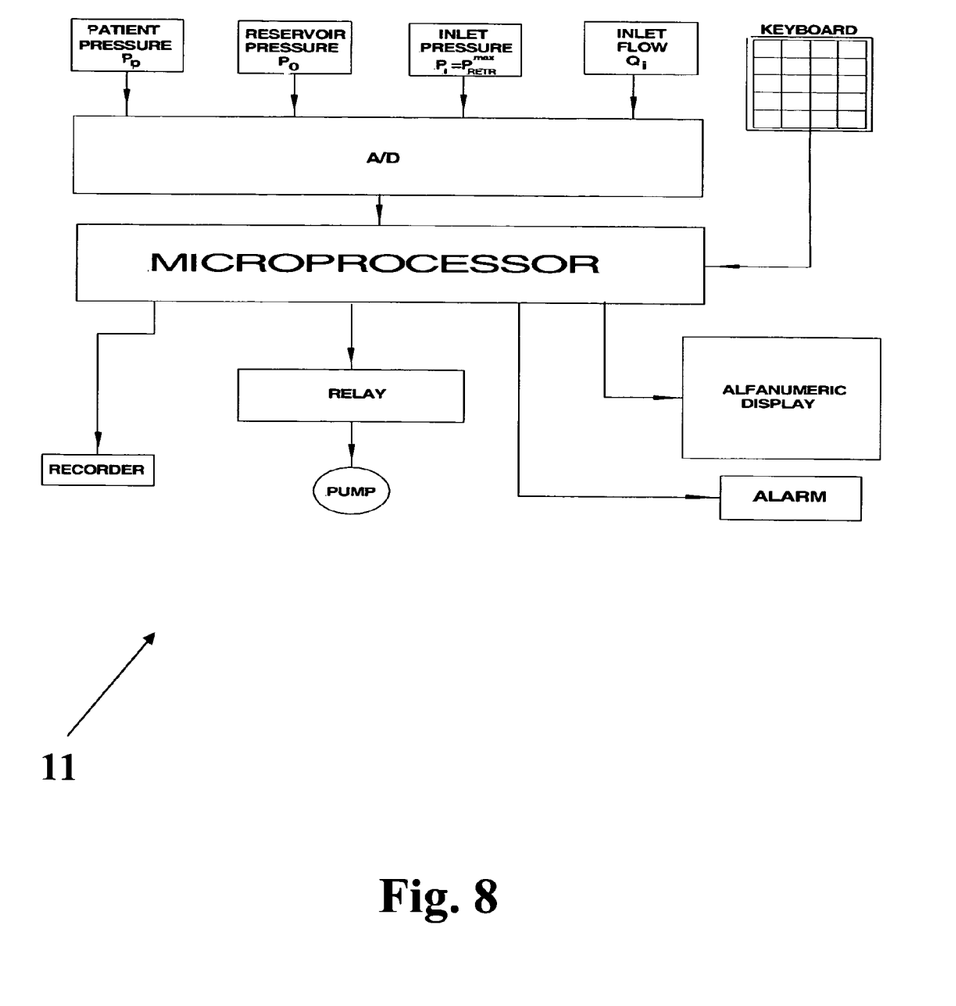
FIG. 8 is schematic diagram of electronic portions of the monitor portion of the Peak Contact Pressure Sensor System (PCPSS).

Looking next at FIG. 8, there is shown one preferred form of the monitor for use with the Peak Contact Pressure Sensor System (PCPSS). The gas monitor is microprocessor based. The data that characterize each type of Peak Contact Pressure Sensor (PCPS) is stored in the microprocessor memory. Such data characterize each type of Peak Contact Pressure Sensor (PCPS). Moreover, this data can be in the form of curve fitting coefficients or lookup tables. An operator, using a keyboard or other input device, indicates the type of Peak Contact Pressure Sensor (PCPS) which is to be used and chooses the monitoring criteria (such as the pressure difference to be tolerated between arterial and brain perfusion pressures, maximum allowed retraction pressure, maximum time allowed for temporary occlusion of local blood supply, etc.) which are to be applied. According to the criteria chosen, the microprocessor may monitor patient arterial blood pressure and adjust reservoir and input pressures by controlling the pump 4. By performing appropriate calibration tests prior to use in surgery, the microprocessor can measure maximum response time of the system. This is important because it should be considered when calculating the maximum time allowed for temporary occlusion of local blood supply before damage occurs. After that, the system will be ready to monitor an actual retraction procedure. Based on these parameters, the microprocessor computes the empirical function or lookup table, which describes the condition of the tissue under retraction. When retraction is too high, the monitor activates an alarm.

In one preferred form of the present invention, the PCPS is made from various plastic films. Since one wall of the PCPS is attached to a rigid wall (i.e., the metal spatula), this wall can be thicker. Alternatively, two plastic thin films can be made of the same materials or different materials; or be of the same or different thickness. As for materials, good candidates are: PVC UHMW, Linear LDPE, Polyester, HDPE, Polyurethane, Polypropylene, Polyzem, EVA, etc., as well as other copolymers. All of them can be obtained in 1 mil thicknesses. Some, such as polyesther films, can be as thin as 0.36 mil.

In another preferred form of the present invention, the separate parts of the Peak Contact Pressure Sensor System (PCPSS) may be joined by various methods. By way of example but not limitation, they can be joined by means of laser welding, direct thermal sealing (hot tool, impulse and hot plate welding], radio frequency (RF) welding, induction welding, ultrasonic welding, etc.

Factors which may influence the operation of the system include: gas viscosity, curvature of the mounted surface which can be done with curved spatulas, width and length of the channel, channel proximity to the edge of the brain retractor, the effect of restriction inserted into output tube, etc.

In addition to the foregoing, the sensor surface may be lined with a moisturizing barrier made out of commercially available layer of cotton. This can be important to prevent injury to the exposed cells. While such a lining will cause an additional pressure drop between the brain and the channel walls of the PCPS, this effect may be taken into account when monitoring retractor pressure.

Alternatively, fluid irrigation may be provided on the working surface between the brain retractor and the brain tissue. In this embodiment of the invention, the Peak Contact Pressure Sensor System (PCPSS) can simultaneously perform two functions: besides detecting maximum local pressure, it may also have a complex channel system which will deliver fluid through perforations.

In addition to the foregoing, the system may be provided with an electronic gas flow sensor, a gas leak detector, and a high sensitivity pressure transducer inserted into inlet tube. This pressure transducer is mounted in such a way that it will sense static pressure only.

The system preferably comprises a desktop PC with I/O module. This I/O module gathers and digitizes signals from an arterial pressure transducer attached to the patient, from the pressure sensor and possibly from the gas flow sensor at the entrance to the Peak Contact Pressure Sensor (PCPS). In addition, the I/O module receives a signal from the pressure transducer, which monitors the pressure in the gas reservoir. The microprocessor then processes the data (including elapsed time as determined by an internal clock) and sends the appropriate signals to the display screen, the alert unit and, via the I/O module, the gas pump and the solenoid valves. In the case of a very small Peak Contact Pressure Sensor (PCPS), it may be desirable to use selected gases, e.g., $CO_2$, and a special gas detector.

As noted above, the Peak Contact Pressure Sensor System (PCPSS) can be used with anatomical retractors other that brain retractors. By way of example but not limitation, it may be employed with retractors of the sort commonly used in bladder procedures, liver vascular surgery, gynecology, organ transplantation, etc.

It should also be appreciated that, while in the foregoing description the Peak Contact Pressure Sensor (PCPS) comprises channels filled with a gas, it is also possible to practice the present invention by filling the channels with an appropriate fluid, e.g., a liquid or a gas.

Interestingly, since the use of retractors can require considerable skills in many medical applications, the Peak Contact Pressure Sensor System (PCPSS) can be a valuable teaching tool.

ADDITIONAL APPLICATIONS

In addition to surgical applications, the Peak Contact Pressure Sensor System (PCPSS) can be employed in many other fields. By way of example but not limitation, the Peak Contact Pressure Sensor System (PCPSS) can be used as the touch sensor for artificial limbs, or for mechanized handling of delicate objects, e.g., the monitoring grip of robotic hand. In essence, the Peak Contact Pressure Sensor System (PCPSS) can be used as a sensor for detection of Peak Contact Pressure for any industrial and research fields.

MODIFICATIONS

It is to be understood that the present invention is by no means limited to the particular construction herein disclosed and/or shown in the drawings, but also comprises any modification or equivalent within the scope of the claims.

What is claimed is:

1. A smart tissue retractor system comprising:
   a retractor;
   at least one channel carried by the retractor and comprising a wall, wherein the wall is configured to deform upon engagement with a force which exceeds a threshold level, and further wherein the channel is filled with a fluid; and
   a monitor for monitoring changes in the flow of the fluid within the at least one channel.

2. A system according to claim 1, wherein the channel is configured to completely collapse upon engagement with a force which exceeds a threshold level.

3. A system according to claim 1, wherein the channel is configured to partially collapse upon engagement with a force which exceeds a threshold level.

4. A system according to claim 1, wherein a plurality of channels are provided, and further wherein the channels have a uniform shape.

5. A system according to claim 1, wherein a plurality of channels are provided, and further wherein the channels have a variable shape.

6. A system according to claim 1 wherein the at least one channel is substantially straight.

7. A system according to claim 1, wherein the at least one channel comprises a tortuous path.

8. A system according to claim 1, wherein a plurality of channels are provided, and further wherein the channels are joined in a serial fashion.

9. A system according to claim 1, wherein a plurality of channels are provided, and further wherein the channels are joined in a parallel fashion.

10. A system according to claim 9, wherein a plurality of channels share a common inlet.

11. A system according to claim 1, wherein the fluid comprises a gas.

12. A system according to claim 1, wherein the fluid comprises a liquid.

13. A system according to claim 1, wherein the monitor comprises an alarm alerting the user of a threshold change in the state of the fluid within the at least one channel.

14. A system according to claim 1, wherein the monitor monitors a change in the pressure of the fluid within the at least one channel.

15. A system according to claim 1, wherein the monitor monitors a change in the flow rate of the fluid within the at least one channel.

16. A system according to claim 1, wherein the fluid comprises a gas and further wherein the monitor comprises a water supply and a passageway connecting the at least one channel to a location beneath the surface of the water supply.

17. A system according to claim 1, wherein the monitor comprises a microprocessor.

18. A system according to claim 1, wherein the at least one passage way comprises a flow restriction.

19. A system according to claim 1, wherein the monitor comprises a pressure transducer for determining the patient's arterial pressure.

20. A system according to claim 1, wherein the wall is configured to deform at a force level lower than that required to cause substantial damage to tissue.

21. A system according to claim 1, wherein the monitor comprises a timer.

22. A system according to claim 1, wherein the monitor is configured to alert the user when a force engaging the wall exceeds a given pressure by more than 70 mm Hg.

23. A system according to claim 1, wherein the wall is configured to deform at a force level lower than that required to cause substantial damage to tissue when the retractor is exerting pressure on the tissue.

24. A method for measuring a force applied to a first object by a second object, the method comprising:
providing at least one channel comprising a wall, wherein the wall is configured to deform upon engagement with a force which exceeds a threshold level, and further wherein the channel is filled with a fluid;
positioning the at least one channel on the first object so that the wall will engage second object; and
monitoring changes in the flow of the fluid within the at least one channel.

25. The method according to claim 24 wherein said first object is human tissue and said second object comprises a retractor having a peak contact pressure sensor that comprises said deformable wall and said at least one channel and also and inlet and outlet for said at least one channel, and further wherein said method comprises flowing said fluid through said at least one channel and generating an alarm responsive to changes in the flow of said fluid as a consequence of deformation of said wall by a force that exceeds said threshold level.

26. The method according to claim 25 wherein said fluid is air or $CO_2$ and is supplied to said inlet at a substantially constant pressure.

27. A smart tissue retractor system comprising:
a surgical retractor;
a peak contact pressure sensor on said retractor, said sensor comprising means defining at least one channel having an inlet and an outlet whereby fluid can flow through said channel, said means comprising a wall that is deformable upon engagement with tissue under a force which exceeds a threshold level; and
means for monitoring changes in the flow of fluid within said at least one channel as said wall is deformed.

28. A system according to claim 27 wherein said wall is configured to deform at a force level lower than that required to cause substantial damage to tissue.

29. A system according to claim 27 further including means for generating an alarm when said wall is deformed by engagement with tissue under a force which exceeds said threshold level.

30. A system according to claim 27 wherein said sensor comprises first and second plastic sheets with said first plastic sheet overlying and being attached to a surface of said retractor and said second plastic sheet being separated from said surface by said first plastic sheet, said first and second plastic sheets being attached to one another and coacting to form said at least one channel, and said second sheet constituting said deformable wall.

31. A system according to claim 30 further including a member disposed between said first and second plastic sheets and coacting therewith to define said at least one channel.

32. A system according to claim 27 wherein said fluid is a gas.

33. A system according to claim 32 wherein said gas is air or $CO_2$.

34. A system according to claim 25 further including means for supplying fluid to said inlet at a constant pressure.

* * * * *